United States Patent

Thust et al.

[11] Patent Number: 5,955,335
[45] Date of Patent: Sep. 21, 1999

[54] BIOMATERIAL IMMOBILIZATION ON AN $Si_3N_4$ SURFACE CONTAINING SI-$NH_2$ GROUPS WITH A HETEROBIFUNCTIONAL CROSS-LINKING AGENT

[75] Inventors: Marion Thust, Köln; Michael J. Schöning, Jülich; Joachim Vetter, Köln; Ulrich B. Kaupp, Aachen; Peter Kordos, Jülich; Hans Lüth, Aachen, all of Germany

[73] Assignee: Foschungszentrum Jülich GmbH, Jülich, Germany

[21] Appl. No.: 08/826,779

[22] Filed: Apr. 7, 1997

Related U.S. Application Data

[63] Continuation-in-part of application No. PCT/DE95/01373, Sep. 30, 1995.

[30] Foreign Application Priority Data

Oct. 8, 1994 [DE] Germany ............................ 44 35 998

[51] Int. Cl.⁶ ........................... C12N 11/14; C12N 11/06; G01N 33/551; C07K 17/14
[52] U.S. Cl. .......................... 435/176; 435/181; 436/524; 436/532; 530/811; 530/816
[58] Field of Search .................... 435/174, 176, 435/180, 181; 436/524, 532; 530/811, 816

[56] References Cited

U.S. PATENT DOCUMENTS

5,234,820  8/1993  Wagner et al. ............................ 435/41

OTHER PUBLICATIONS

Jimbo, et al., Chemical Abstracts 109:89013, 1988.
Jimbo, et al., Journal of Molecular Electronics, vol. 4, 1988, pp. 111–118.

Primary Examiner—David M. Naff
Attorney, Agent, or Firm—Klaus J. Bach

[57] ABSTRACT

Biomaterial such as an enzyme, cell, antigen or antibody is immobilized by covalent bonding to a substrate having an $Si_3N_4$ surface containing Si—$NH_2$ groups that provide reactive $NH_2$ groups. A heterobifunctional cross-linking agent having an $NH_2$-reactive group and a biomaterial-reactive group is reacted with the $NH_2$ groups of the surface and then with the biomaterial or the heterobifunctional cross-linking agent is reacted with the biomaterial and then with the $NH_2$ groups of the surface. The $Si_3N_4$ surface containing Si—$NH_2$ groups can be formed by precipitating on a substrate a 10–1000 nm thick $Si_3N_4$ layer from a $SiH_4/NH_3$ mixture, and providing reactive $NH_2$ groups on the surface of the layer by subjecting the surface to hydrolyzing cleaning.

6 Claims, 3 Drawing Sheets

BIOMATERIAL IMMOBILIZATION ON AN SI₃N₄ SURFACE CONTAINING SI-NH₂ GROUPS WITH A HETEROBIFUNCTIONAL CROSS-LINKING AGENT

This is a CIP application of International Patent Application PCT/DE95/01373, filed Sep. 30, 1995, designating the U.S. and claiming the priority of German application P 44 35 998.51 filed Oct. 8, 1995.

BACKGROUND OF THE INVENTION

The invention relates to a method of immobilizing biomaterial on a substrate with an $Si_3N_4$ surface to which the biomaterial is covalently bonded by means of a bonding agent.

The immobilization of biomaterial is of substantial importance for the utilization of bioactivity particularly under liquid contact. It is very important in chemical processes as well as for an analysis in separating processes or for the recurrent utilization of the biofunction. Other areas of interest are in the pharmaceutical area, in medicine, and in environmental sciences.

Many attempts have been made to immobilize biomaterial on different surfaces, also mineral surfaces such as glass which generally is first silanized.

E. Tamiya et al, describe in the J. Mol. Cartal. 43(1988) 293–301, an immobilization of urease on a quartz crystal with a thin silver layer onto whose surface a silicon nitride layer is sputtered. The so treated crystal was stored in air for 24 hrs, was then washed and dried in air. Subsequently, γ-aminopropyltriethoxysilane and then glutaraldehyde were vapor deposited on the surface. The so-generated thin organic surface film of about 100 A thickness is considered to have little porosity. A bonding of the silane and the aldehyde cannot clearly be observed.

The enzyme deposited on the film from an aqueous solution had an activity relative to the free urease of only 2.25%. This immobilization procedure does not appear to be fully satisfying.

It is the object of the present invention to provide a new type of biomaterial immobilization which requires only a small number of treatment steps and which provides relatively stable products in a reproducible manner.

SUMMARY OF THE INVENTION

In a method for the immobilization of biomaterial on a substrate a $Si_3N4$ surface with bonding-active $NH_2$ groups is provided on the immobilization substrate and a heterobifunctional cross-linking agent with $NH_2$ reactive aldehyde-, ester-, halogenide-, epoxide-, imine-, or isocynate group is reacted with the $NH_2$ groups on one hand and a biomaterial reactive group on the other, to which the biomaterial is then bonded.

The invention is suitable for the immobilization of enzymes, microorganisms, cells, antibodies, antigens, organelles, tissue sections etc., on substrates such as semiconductor substrates, foils, wall surfaces, granulates, building components, particularly of a mineral type, and is useful in applications as mentioned initially.

Silicon nitride surfaces can be provided, among others, by means of CVD techniques, by precipitation out of a $SiH_4$/$NH_3$—mixture (see A.Garde et al., ESSDERC 1994-11-15 of September. 1994, Ed. C. Hill & P.Ashburn). They absorb oxygen from the air and, under humid conditions, tend to hydrolyze while forming Si—OH, Si—NH and Si—NH₂ groups. These groups can be utilized as reactive functions for the bonding of biomaterials, by way of crosslinking agents, to the nitride surface.

It is particularly suitable with the method according to the invention to utilize an $Si_3N_4$ surface from which oxygen has been removed by treatment with hydrofluoric acid and provide for a covalent enzyme bonding in two steps wherein a crosslinking agent is selected whose one function reacts first with the $NH_2$ groups or with the NH groups of the nitride surface and whose second function is used to subsequently react with protein. Alternatively, the crosslinking agent may first be made to react with the protein and this product may then be caused to react with the $Si_3N_4$ surface.

As $NH_2$ reactive groups of the crosslinking agent particularly aldehyde-, halogenide-, epoxide-, imide-, or isocyanate functions may be used. A plurality of reaction possibilities with amino groups are presented for example in U.S. Pat. No. 5,234,820. For practical use, various compounds are already offered by the firm Pierce in the "Immuno Technology Catalog and Handbook" of 1992/3.

For reaction with the biomaterial, crosslinking agent functions are utilized which are capable of covalent boding by way of functional groups of the enzyme, particularly with terminal carboxyl groups or side chain groups such as —Sh, —COOH, or —OH groups or aromatic rings. In accordance with the invention, the bonding of the biomaterial to the nitride surfaces is aimed at by utilizing a heterobifunctional crosslinking agent. In this connection, a heterobifunctional crosslinking agent is considered to be also such a crosslinking agent which has two chemically essentially identical functions, however, with different reactivity toward the different reaction partners.

The heterobifunctional crosslinking agents react step-by-step with the $Si_3N_4$ surface and then with the protein. The amino-specific reactions given below occur at room temperature with a neutral to slightly alkaline pH value. An increase in the temperature or in the pH value increases the reaction speed, but also the hydrolysis rate of the crosslinking agent. The buffer used should contain neither amines nor any other compounds with which the functional groups of the crosslinking agent could react.

N-hydroxysuccinimidoester reacts specifically with primary amines. During the reaction, N-hydroxysuccinimide is released and an amide bond is established between the primary amine and the rest group of the ester utilized. If no water soluble analogen is used, a crosslinking agent which includes this functional group must first be dissolved in a small amount of an organic solvent (for example DMSO). Only then is it diluted to the final concentration in an aqueous buffer. The ion strength of the buffer should not be too high in order to avoid crystallization effects. A slightly alkaline pH value (7–9) guarantees that the primary amines are in an unproportioned state.

Aldehyde has a strongly reducing carbonyl group which reacts with primary amines while forming water. The reaction of primary amines with imido esters occurs in a pH range of between 8 and 9. The ester is freed in the process and the primary amine forms with the imido group a guandino compound.

The bonding to the protein is now achieved by way of the second group of the functional group of the crosslinking agent which is still free. This group can react specifically or non-specifically with thiol-, carboxyl-, or carbohydrate groups of the protein.

If the crosslinking agent includes as second functional end a thiol-specific group such as malenide, an activated halogenide or pyridylsulfide, the protein to be bonded must include a sulfhydryl group (usually from a (cysteine rest). If this should not be available, it can be generated by reduction of protein sulfides. Alternatively, primary amines of the protein can be so modified that sulfhydryl groups are available (Trauts reagent). In order to prevent the oxidation of this group, the buffer used must be degasified. The addition of the complex former EDTA prevents the oxidation by metals which may be present in the solution.

Maleimide reacts in slightly sour to neutral environment (pH 6.5–7.5) whereas for halogenides and pyridyldisulfide pH values greater than or equal to 7 are to be recommended.

Glycolized proteins can be crosslinked at the carbohydrate side chains by way of hydroxy groups. If a carbohydrate active crosslinking agent is used which includes as functional group for example a hydrazide, the carbohydrate groups of the protein must first be oxidized to an aldehyde (for example, with $NaIO_4$).

The carbonyl group then formed reacts with the hydrozite to form semicarbazone.

It is possible to generate a bond between carboxy and amino groups by a reaction with carbodiimides. In the sour pH range (4–5), the carbodiimides convert the carboxy group into an active ester bond. This reacts with primary amines while forming an amide bond and freeing urea.

When using crosslinking agents whose non-amino-specific functional end includes a photoactivatable group (for example, azidophenyl), the immobilization process must take place in a dark room with only red light. The azidogroup of azidophenyl is activated by exposure to light with a wave length of 265–275 nm.

The invention can be used for the bonding of very different biomaterials to substrates or any carrier. It was tested for example specifically with penicillin sensors. For this reason, the subsequent description refers to such sensors. Reference is made in the following description to the attached drawings. They show schematically:

DESCRIPTION OF A PREFERRED EMBODIMENT

Example:

An electrically nonconductive layer of silicon oxide of the thickness of 5–100 nm was first deposited on p or, respectively, p$^+$-doped silicon wafers (1 mohmxcm–30 Ohmxcm) by thermal dry-oxidation between 700 and 1200° C. (here at 1000° C.) in a diffusion furnace. Then non-condutive silicon nitride with a thickness of 10–100 nm was applied by chemical deposition in a gas phase (PCEVD). The ratio $SiH_4/NH_3$ in the reaction gas was 2/1, the substrate temperature was 200–500° C. (here 300° C.) and the pressure during the deposition was 1–3 Torr (here 1.5 Torr). An annealing step followed under $N_2$ atmosphere (5–60 minutes at 700–1000° C.). Finally, an ohm-type contact (for example 10–1000 nm Al, Au) was applied to the unpolished substrate side. The material used was applied by thermal vapor deposition in a vacuum at a basic pressure $<10^{-5}$ mbar. The deposition rate was between 0.1 and 10 nm/s. Subsequently, the wafer was annealed in a RTA furnace at 150–500° C. (here 400° C.) in an $N_2$ atmosphere.

Immediately before the start of the enzyme immobilization process, the wafers were cleaned in acetone, 2-propanol and distilled water in an ultrasonic bath and were then etched for 10–60 sec (here 30 sec) in diluted hydrofluoric acid (1–10% HF).

With the use of the heterobifunctional crosslinking agent ANB-NOS(N-5-Azido-2-nitrobenzoyloxysuccinimide) the crosslinking agent was first dissolved in a small amount of DMSO and then diluted with 0.2M triethanolamine buffer (pH 5–9) to an end concentration of 0.5–10 mM. the solution was applied to the $Si_3N_4$ surface and incubated for 5 to 40 minutes at room temperature. At lower temperature, the incubation time is longer. Molecules not bonded to the silicon nitride surface were removed by flushing with triethanolamine buffer (TEA). Then the enzyme (penicillinase type I from the Bacillus Cereus, Sigma P0389) was dissolved (1000–5000 unit/ml) in a buffer which does not contain any amino groups (for example, TEA, particularly not TRIS- or glycine buffer) and deposited on the silicon nitride surface pretreated with a crosslinking agent. After an incubation time of 1–240 min (here 15 min) at temperatures of 4 to 60° C., particularly at room temperature, the bonding of the enzyme molecules to the still free functional group of the crosslinking agent was induced by light in the wave length range of 320–350 nm. After completion of the immobilization process, the finished penicillin sensors were washed with 0.1 MTRIS-buffer (pH7–8) and distilled water and were dried for at least 10 minutes in air or under an $N_2$ or inert gas atmosphere.

With field effect sensors, so made measurements for determining the penicillin concentration in aqueous solutions were performed.

Figure 1:
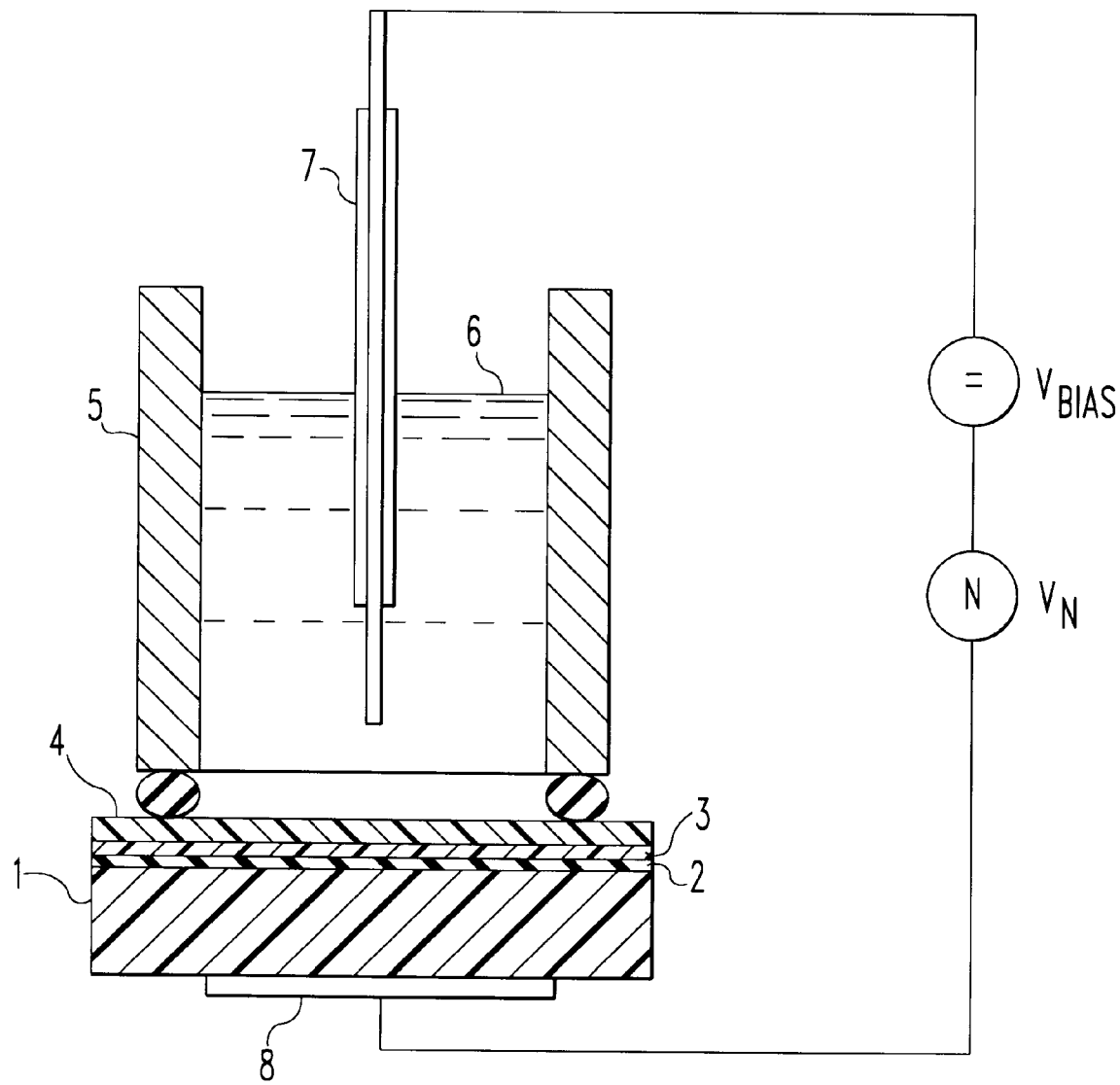
FIG. 1, a sensor principle (measuring arrangement)

FIG. 1 shows schematically the measuring arrangement. The field effect sensor made in accordance with the invention which consists of the silicon substrate 1, the insulating layer 2 (silicon dioxide and silicon nitride), the crosslinking agent layer 3 and the enzyme layer (penicillin layer) 4 was integrated into a measuring cell. The measuring cell was filled with a measuring solution which contained penicillin G in a concentration of $10^{-5}$ to 1 mol/l. A reference electrode (for example, Ag/AgCl) extends into the measuring solution 6. The potentials are measured by way of the reference electrode 7 and a contact electrode 8 on the silicon substrate.

Figure 2:
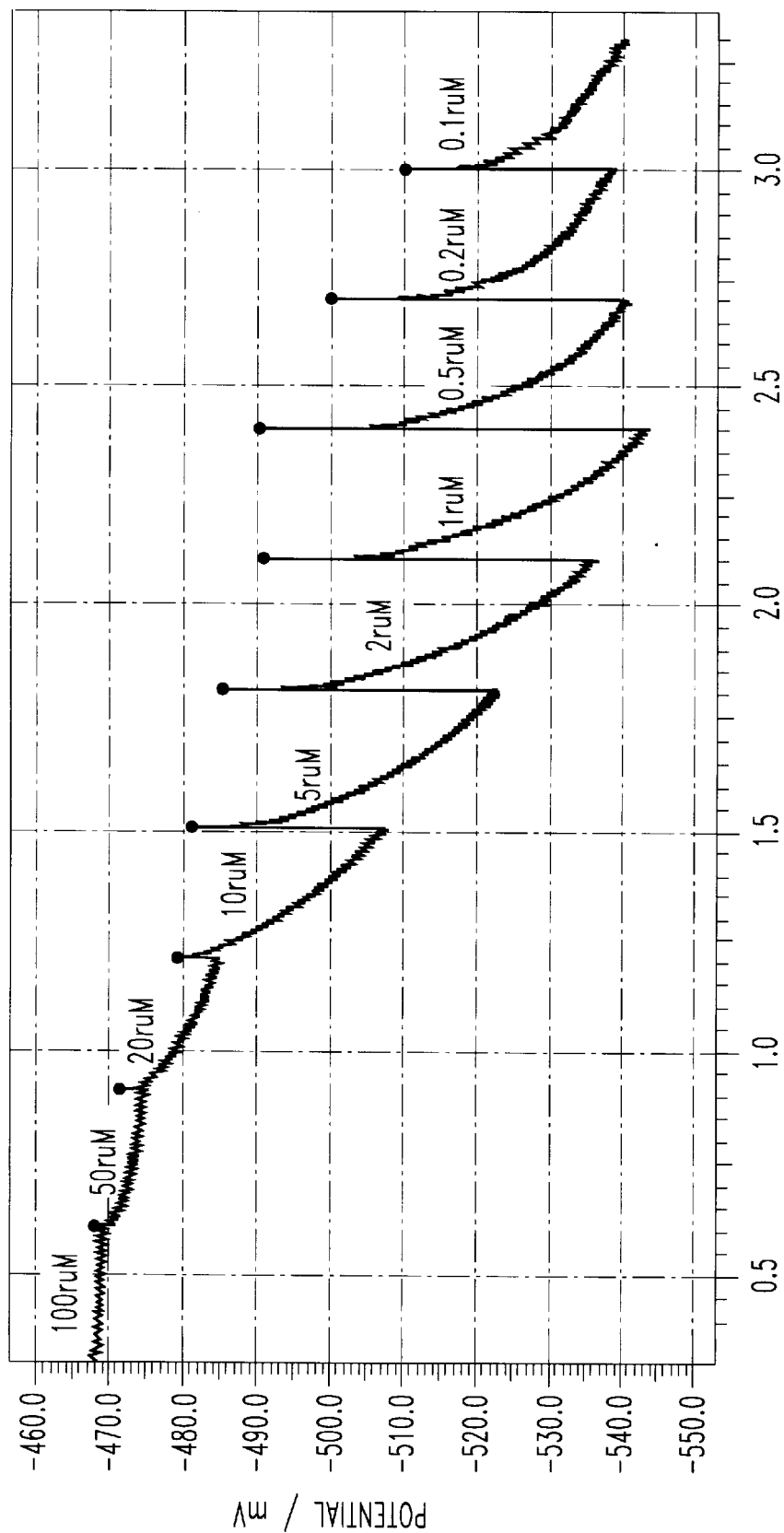
FIG. 2, a typical measurement curve for a concentration range of $10^{-4}$ to $10^{-1}$ mole/l penicillin and FIG. 3 a calibration curve of a sensor according to the invention.

FIG. 2 shows a typical measurement curve which was taken in the CONCAP (CONstant CAPacitance) mode in a concentration range of $10^{-4}$ to $10^{-1}$ mol/l of penicillin. Penicillin G sodium salt (Sigma P3032) was dissolved for this purpose in 10 mM TRISHCl buffer, pH 7. With increasing penicillin concentration, the concentration of the formed penicillo acid and, consequently, the concentration of the hydrogen ions in close proximity of the silicon nitride surface acting as pH transducer increases. This results in a shifting of the potential at the interface silicon nitride/electrolyte toward more positive or respectively, more negative voltage values. The plotting of the values over time permits the observation of the concentration-dependent potential curve of the enzyme reaction. The measuring solutions were changed at the indicated intervals.

Figure 3:
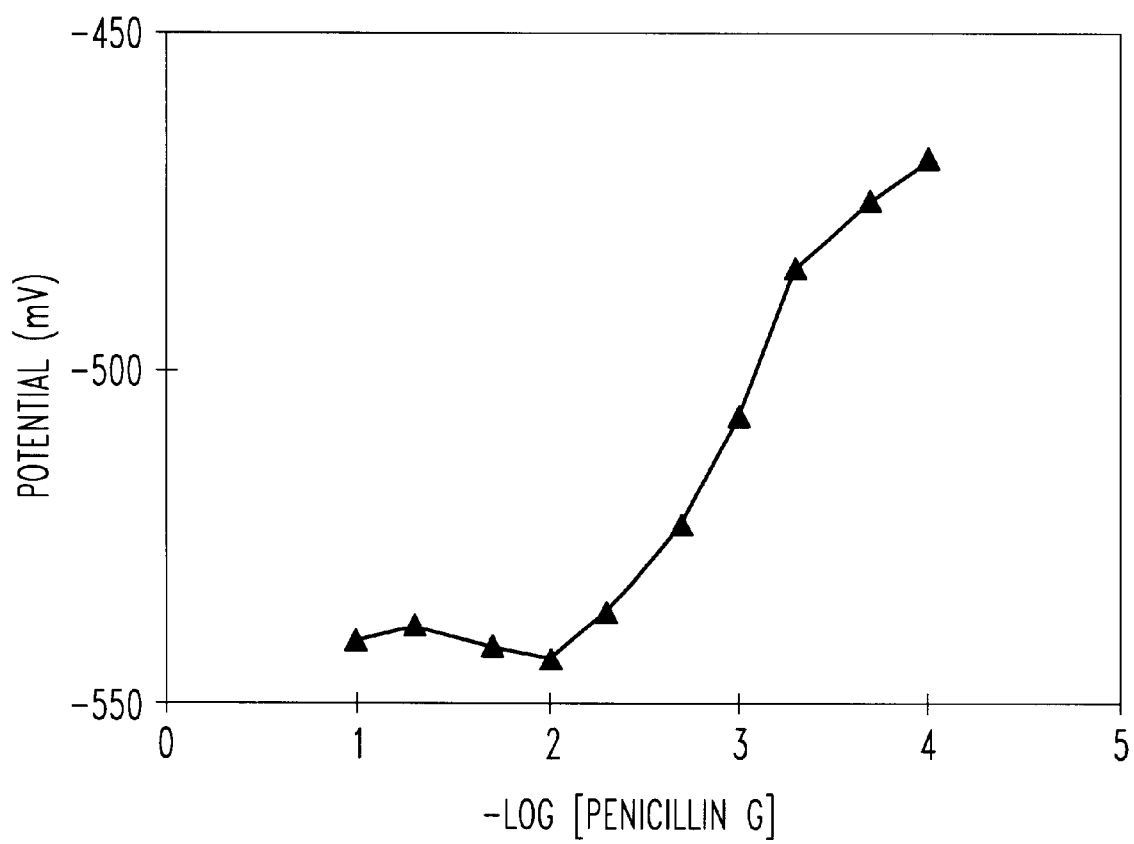

FIG. 3 shows the chemical transmission characteristic determined from FIG. 2. It represents the calibration curve of the field effect sensor made in accordance with the invention. Details with respect to the sensitivity of a potentiometric chemo- or biosensor with respect to the basic Nernst relation are given in the linear range of the curve, that is, in the range in which there is a logarithmic relation between the penicillin concentration and the potential present. With the sensor made in accordance with the invention, this range is between p-penicillin 2,3 and 3,3 corresponding to 0.5 to 5 mM. The sensitivity is 50 mV per decade.

The exact location of the linear measurement range and the absolute sensitivity depend to a large extent on the selection of the buffer composition, its concentration, that is the buffer capacity, and the pH value. By a suitable selection of these parameters, the measurement range required for a particular measurement can be accurately adjusted. For example, using an IMIDAZOL buffer (pH7), the linear measurement range is between 2 and 20 in M penicillin; with a HEPES buffer, it is about between 1 and 10 mM. Increasing the pH value shifts the location toward higher penicillin concentrations, reducing the pH value shifts it correspondingly to lower concentrations.

The sensors made in accordance with the invention have a high time stability of more than 250 days. The sensitivity is in the area of 50 mV per penicillin decade.

The manufacture of a field effect transistor which has in the gate area the same makeup as the capacitive layer arrangement described by the invention is possible.

What is claimed is:

1. A method for the immobilization of biomaterial on a substrate with an $Si_3N_4$ surface to which the biomaterial is covalently bonded by means of a hetero-bifunctional cross-linking agent, said method comprising the steps of:

providing a substrate with a $Si_3N_4$ surface having Si—$NH_2$ groups to provide reactive $NH_2$ groups, providing a hetero-biffinctional cross-linking agent having an $NH_2$-reactive group selected from the group consisting of aldehyde, ester, halogenide, epoxide, imine and isocyanate, and a biomaterial-reactive group, reacting the $NH_2$-reactive group of the cross-linking agent with the $NH_2$ groups of the $Si_3N_4$ surface to covalently bond the cross-linking agent to the surface, and reacting a biomaterial with the biomaterial-reactive group of the cross-linking agent to covalently bond the biomaterial to the cross-linking agent and immobilize the biomaterial on the $Si_3N_4$ surface of the substrate.

2. A method according to claim 1, wherein said biomaterial reactive group of the cross-linking agent reacts with terminal or side chain groups of proteins.

3. A method according to claim 1, wherein said biomaterial-reactive group of the cross-linking agent reacts with a group selected from the group consisting of carboxyl, sulfhydryl and hydroxyl, or with an aromatic ring.

4. A method according to claim 1, wherein said $Si_3N_4$ surface is formed by precipitating onto the substrate a 10–1000 nm thick $Si_3N_4$ layer from a $SiH_4/NH_3$ mixture, and providing reactive $NH_2$ groups on the $Si_3N_4$ surface by subjecting the surface to hydrolyzing cleaning.

5. A method according to claim 1, wherein said biomaterial is selected from the group consisting of enzymes, microorganisms, cells, antibodies, antigens, organelles and tissue sections, and said substrate is selected from the group consisting of foils, wall surfaces and granulates.

6. A Method for the immobilization of biomaterial on a substrate with an $Si_3N_4$ surface to which the biomaterial is covalently bonded by means of a hetero-bifunctional cross-linking agent, said method comprising the steps of providing a substrate with a $Si_3N_4$ surface having Si—$NH_2$ groups to provide reactive $NH_2$ groups, providing a hetero-bifunctional cross-linking agent having an $NH_2$-reactive group selected from the group consisting of aldehyde, ester, halogenide, epoxide, imine and isocyanate, and a biomaterial-reactive group, reacting a biomaterial with the biomaterial-reactive group of the cross-linking agent to covalently bond the biomaterial to the cross-linking agent, and reacting the $NH_2$-reactive group of the cross-linking agent with the $NH_2$ groups of the $Si_3N_4$ surface to covalently bond the cross-linking agent to the surface and mobilize the biomaterial on the $Si_3N_4$ surface of the substrate.

* * * * *